(12) United States Patent
Anosov et al.

(10) Patent No.: US 7,890,161 B2
(45) Date of Patent: Feb. 15, 2011

(54) METHOD FOR DETECTING THE MYOCARDIAL STATE OF THE HEART AND A MEASURING APPARATUS FOR PERFORMING THIS METHOD

(75) Inventors: Oleg Anosov, Erlangen (DE); Ildar Khassanov, Erlangen (DE)

(73) Assignee: Biotronik CRM Patent AG, Baar (CH)

( * ) Notice: Subject to any disclaimer, the term of this patent is extended or adjusted under 35 U.S.C. 154(b) by 701 days.

(21) Appl. No.: 11/933,795

(22) Filed: Nov. 1, 2007

(65) Prior Publication Data

US 2008/0119746 A1    May 22, 2008

(30) Foreign Application Priority Data

Nov. 18, 2006  (DE) .................. 10 2006 054 474

(51) Int. Cl.
*A61N 1/08* (2006.01)
(52) U.S. Cl. .................. 600/517; 600/518; 607/126; 607/130
(58) Field of Classification Search ......... 607/119–132; 600/517, 515, 518
See application file for complete search history.

(56) References Cited

U.S. PATENT DOCUMENTS 5,740,811 A    4/1998   Hedberg et al.
5,782,885 A    7/1998   Andersson
6,615,082 B1   9/2003   Mandell

FOREIGN PATENT DOCUMENTS

WO    WO 2005042090    5/2005

OTHER PUBLICATIONS

Altunkeser, Bülent B; et al. "Can P waveparameters obtained from 12-lead surface electrocardiogram . . . " Angiology, V. 54, No. 4, 2003, Westminister Publications, Inc., NY, US.
German Search Report, dated Jun. 20, 2007.
European Search Report, dated Mar. 18, 2008.

*Primary Examiner*—Mark W Bockelman
*Assistant Examiner*—Erica Lee
(74) *Attorney, Agent, or Firm*—ARC IP Law, PC; Joseph J. Mayo

(57) ABSTRACT

A method for detecting the myocardial state of a heart with a measuring apparatus which includes inserting a bipolar cardiological measuring electrode (4) into a heart division (8) at an acute attachment angle (9) on the myocardium (6) of less than 90°, measuring a cardiological stimulation signal such as an IEGM in sequential cardiac cycles, and in addition, determining the positive and negative maximum amplitudes $V_p$ and $V_n$ of the IEGM, ascertaining an asymmetry factor $\eta$ of the stimulation signal (IEGM) of sequential cardiac cycles according to the equation $\eta=(V_p-|V_n|)/(V_p+|V_n|)$ and storing the asymmetry factor $\eta$ of sequential cardiac cycles for analysis.

14 Claims, 2 Drawing Sheets

US 7,890,161 B2

METHOD FOR DETECTING THE MYOCARDIAL STATE OF THE HEART AND A MEASURING APPARATUS FOR PERFORMING THIS METHOD

This application takes priority from German Patent Application DE 10 2006 054 474.9 filed 18 Nov. 2006, the specification of which is hereby incorporated herein by reference

BACKGROUND OF THE INVENTION

1. Field of the Invention

The present invention relates to a method for detecting the myocardial state of the heart and a measuring apparatus for performing this method.

2. Description of the Related Art

Cardiological experiments and studies have resulted in the finding that the change of the state of the myocardium frequently results in a change of the direction of the excitation propagation of the cardiological stimulation signals in the heart. This is based, for example, on the different velocities of the excitation propagation in healthy myocardial areas on one hand and, for example, in myocardial areas subject to ischemia on the other hand. A further reason may be the change of the geometry of the heart divisions in the event of cardiac insufficiency or cardiomyopathy, in the event of operational wounds, or in the event of a myocardial infarction. Furthermore, direction changes of the excitation propagation may occur due to a change of the myocardial state before a cardiac flutter or also due to psychological stress situations and strains.

Disturbances of this type may be recognized in principle by complex analyses of cardiological stimulation signals, however, complex multi-electrode measurements are known to be necessary for this purpose, as are performed in an ECG, for example. The corresponding measurement methods and apparatuses may not be implemented in practice in an implant.

BRIEF SUMMARY OF THE INVENTION

Proceeding therefrom, the present invention is based on the object of specifying a method for detecting the myocardial state of the heart and a corresponding measuring apparatus, which may be implemented using simple measuring technology and design and may therefore be implemented in an implant.

This object is achieved in regard to the method by the method steps specified as follows:
- inserting a bipolar cardiological measuring electrode in a heart division at an acute attachment angle of the measuring electrode on the myocardium of less than 90°,
- measuring a cardiological stimulation signal in sequential cardiac cycles,
- determining the positive and negative maximum amplitudes $V_p$ and $V_n$ of the stimulation signal of sequential cardiac cycles,
- ascertaining an asymmetry factor η of the stimulation signal of sequential cardiac cycles according to the equation $$\eta = (V_p - |V_n|)/(V_p + |V_n|) \text{ and}$$

storing the asymmetry factor η of sequential cardiac cycles for its analysis.

As will be explained in greater detail on the basis of the exemplary embodiment, the present invention proceeds from the finding that in the event of a measuring electrode which is atypical per se and is not placed perpendicularly to the myocardial plane, the change of the direction of the excitation propagation results in a change of the asymmetry of intracardial electrical signals ("IEGM" in short in the following). The present invention makes use of this in that the specified acute attachment angle of the measuring angle is selected as significantly below 90° and preferably approximately 45°. The specified asymmetry factor may be determined from the corresponding stimulation signals and stored for the subsequent diagnosis of its myocardial state, which is not part of the method according to the present invention, in particular for diagnosis of myocardial ischemia and cardiac insufficiency.

A specific IEGM is used depending on the placement of the measuring electrode in a heart division, thus, for a measuring device placed in the ventricle, the R wave is used, and for a measuring electrode placed in the atrium, the P wave of the cardiological stimulation signal is used.

A corresponding measuring apparatus for performing the method described above thus has:
- a measuring electrode (4), which may be positioned in a heart division (8) at an acute attachment angle (9) to the myocardium (6), and
- an implantable processing apparatus (2), which picks up the measured signals (IEGM) of the measuring electrode (4), for recording, detecting, relaying, and/or analyzing the measured signals to ascertain the asymmetry factor η.

Devices for diagnosing the myocardial state may thus be conceived on the basis of the analysis of the asymmetry factor of the IEGM signals. The simplicity of the method and in particular the slight output signals necessary for this purpose, in the form of the positive and negative maximum amplitudes of a stimulation signal, allow the corresponding method to be applied in modern implantable devices. Preferably, a cardiac pacemaker or defibrillator is thus provided with an integrated analysis apparatus to ascertain the asymmetry factor η.

Alternatively or additionally thereto, the processing apparatus of the measuring apparatus may have a transmitter for relaying the ascertained measured signals to an external analysis station, in which the asymmetry factor η may then be ascertained.

BRIEF DESCRIPTION OF THE FIGURES

Further features, details, and advantages of the present invention may be inferred from the following description, in which an exemplary embodiment of the method according to the present invention and a corresponding measuring apparatus are explained in greater detail.

DETAILED DESCRIPTION OF THE INVENTION

Figure 1:
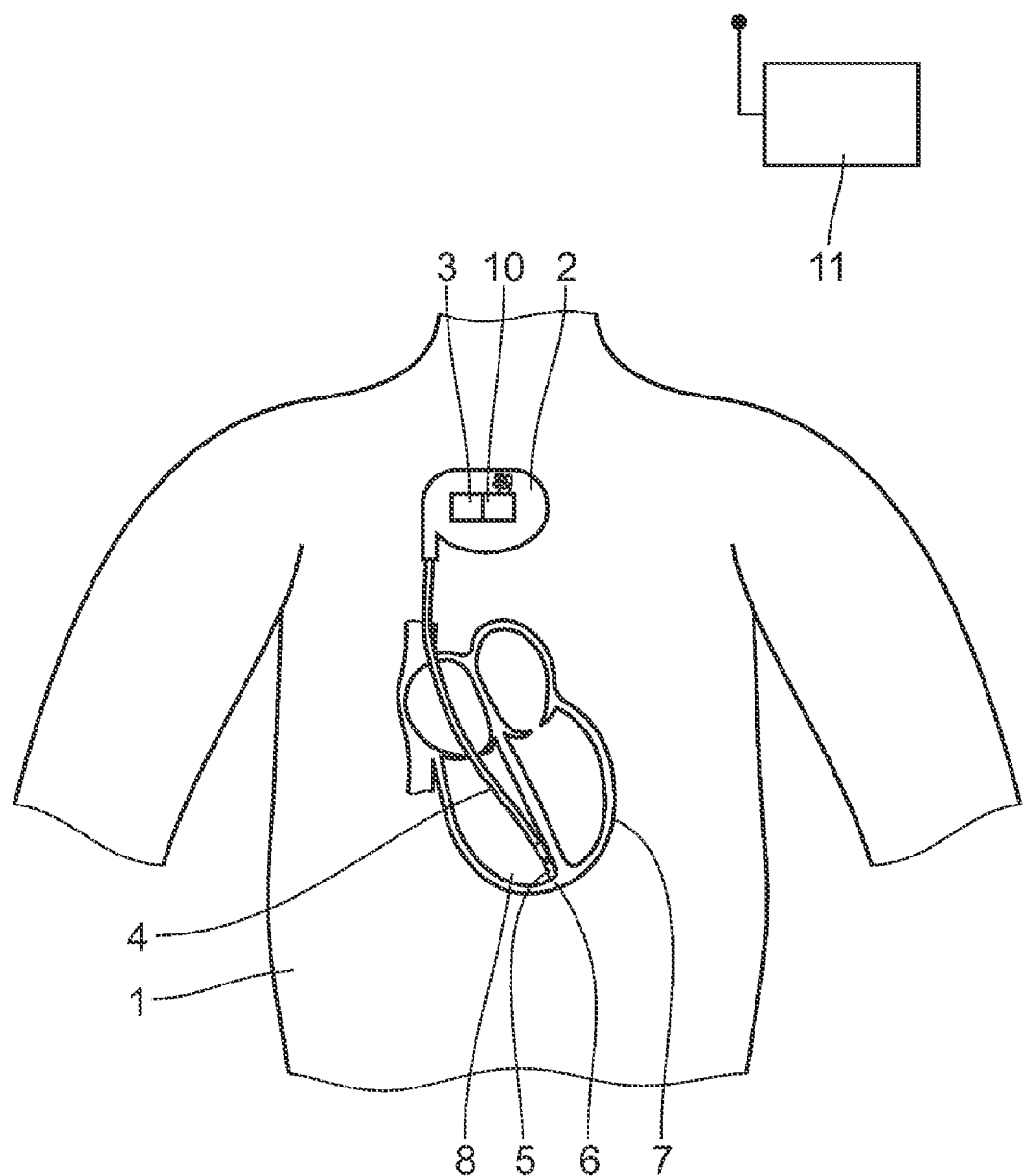
FIG. 1 shows a schematic view of a patient thorax having an implanted cardiac pacemaker and measuring electrode in the right ventricle.
Figure 2:
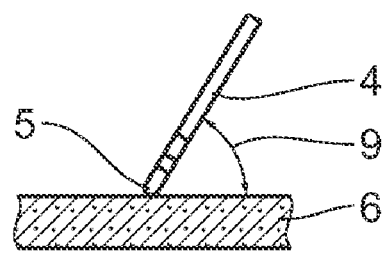
FIG. 2 shows a schematic enlarged view of the measuring electrode anchored in the myocardium.

FIG. 1 shows a cardiac pacemaker 2 implanted in the thorax 1 of a cardiac patient, in which an analysis apparatus 3 for the above-mentioned asymmetry factor η, which is to be explained in greater detail below, is integrated. This analysis apparatus 3 processes the measured signals of the bipolar measuring electrode 4, whose electrode tip 5 is anchored in the myocardium 6 of the heart 7 in the area of the right ventricle 8. As FIG. 2 shows, the measuring electrode 4 is inclined at an acute angle 9 of approximately 45° to the plane of the myocardium 6.

The measured signals of the measuring electrode 4 or data generated by the analysis apparatus 3 may be transmitted via the transmitter 10 to an external analysis station 11, where it may be processed further and used in the course of so-called "home monitoring", for example.

Figure 3:
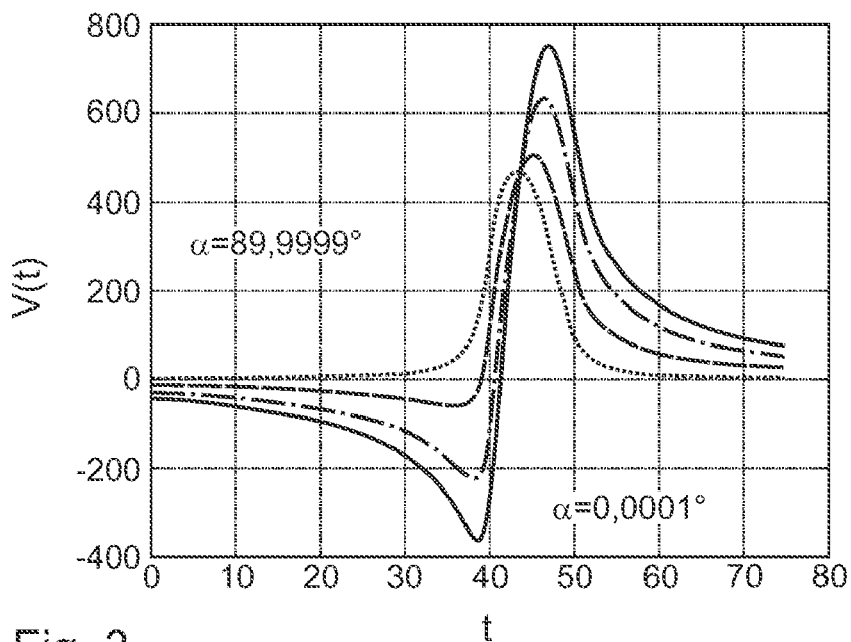
FIG. 3 shows a diagram of analytically calculated IEGM signals for various directions of the excitation propagation.

Analytical evaluations of medical experiments have shown that in the event of non-perpendicular positioning of the measuring electrode 4 to the plane of the myocardium 6, a change of the direction of the excitation propagation results in a change of the asymmetry of intercardial electrical signals. FIG. 3 shows IEGM signals calculated for several angles α between the direction of the excitation propagation and the projection of the measuring electrode 4 on the myocardial surface.

Figure 4:
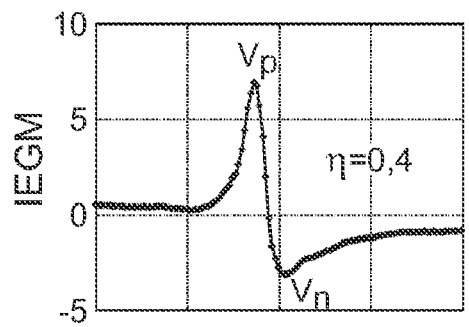
FIGS. 4 and 5 show IEGM signals having different asymmetries.
Figure 5:
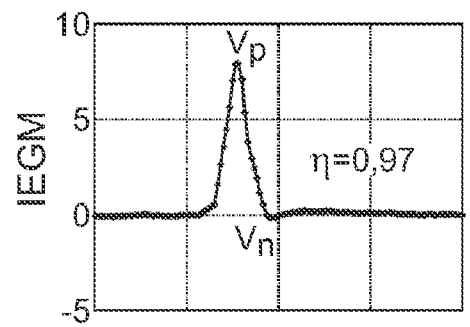

FIGS. 4 and 5 show IEGM signals in the form of R waves of the measuring electrode 4 inserted into the right ventricle as shown in FIG. 1. The amplitude $V_p$ of the positive wave and the amplitude $V_n$ of the negative wave of the particular signal are plotted. According to the equation $$\eta = (V_p - |V_n|)/(V_p + |V_n|)$$

the asymmetry factor η is calculated in FIG. 4 as η=0.4 and in FIG. 5 as η=0.97.

Figure 6:
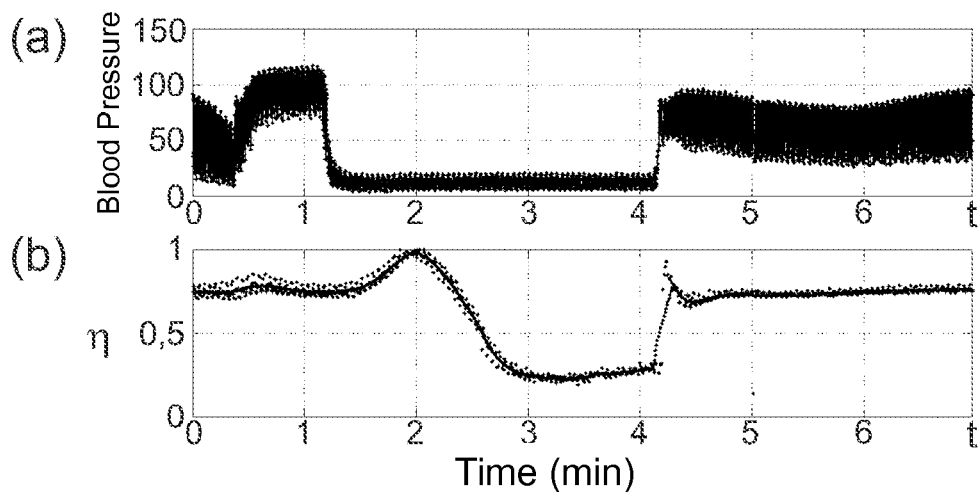
FIG. 6 shows a time diagram of the blood-pressure (a) and the corresponding IEGM asymmetry factor η (b).

The significance of the asymmetry factor η for a pathological situation of the heart may be shown on the basis of FIG. 6. The diagram of (a) shows the blood pressure in the coronary artery during an ischemia, which occurs in a period of time between approximately t=1 minute and t=4 minutes.

With a brief delay, the asymmetry factor η plotted in partial figure (b) passes through a maximum at t=2 minutes, to then sink significantly to a value of approximately a third of the original asymmetry factor.

The significance of the change of the asymmetry factor for the presence of an ischemia is clear.

What is claimed is:

1. A method for detecting the myocardial state of a heart comprising:
    inserting a bipolar cardiological measuring electrode into a heart division and anchoring a tip of the electrode in a myocardium of the heart at an attachment angle of less than 90°, relative to a myocardial surface;
    measuring a signal of sequential cardiac cycles via intracardiac electrogram to collect measured signals with an implantable processing apparatus;
    determining positive and negative maximum amplitudes $V_p$ and $V_n$ of said signal of sequential cardiac cycles;
    ascertaining an asymmetry factor η of said signal of sequential cardiac cycles according to $\eta=(V_p-|V_n|)/(V_p+|V_n|)$; and
    storing said asymmetry factor η of sequential cardiac cycles for analysis.

2. The method according to claim 1 further comprising:
    determining the positive and negative maximum amplitudes $V_p$ and $V_n$ of said signal of sequential cardiac cycles with said implantable processing apparatus;
    ascertaining the asymmetry factor η of said signal of sequential cardiac cycles according to equation $\eta=(V_p-|V_n|)/(V_p+|V_n|)$ with said implantable processing apparatus; and
    storing the asymmetry factor η of sequential cardiac cycles for analysis with said implantable processing apparatus.

3. The method according to claim 1 further comprising:
    transmitting the measured signals to an external analysis station via a transmitter coupled with said implantable processing apparatus;
    determining the positive and negative maximum amplitudes $V_p$ and $V_n$ of said signal of sequential cardiac cycles with said external analysis station;
    ascertaining the asymmetry factor η of said signal of sequential cardiac cycles according to equation $\eta=(V_p-|V_n|)/(V_p+|V_n|)$ with said external analysis station; and
    storing the asymmetry factor η of sequential cardiac cycles for analysis with said external analysis station.

4. The method according to claim 1 wherein said anchoring comprises anchoring said bipolar cardiological measuring electrode at an attachment angle of approximately 45°.

5. The method according to claim 1 further comprising inserting said bipolar cardiological measuring electrode into a ventricle of said heart and measuring an R wave of said intracardiac electrogram with said bipolar cardiological measuring electrode.

6. The method according to claim 1 further comprising inserting said bipolar cardiological measuring electrode into an atrium of said heart and measuring a P wave of said intracardiac electrogram with said bipolar cardiological measuring electrode.

7. A measuring apparatus for detecting the myocardial state of a heart comprising:
    a bipolar cardiological measuring electrode configured to insert into a heart division and configured to anchor a tip of the electrode in a myocardium of the heart at an attachment angle of less than 90°, relative to a myocardial surface;
    an implantable processing apparatus configured to measure a signal of sequential cardiac cycles via intracardiac electrogram to collect measured signals;
    wherein the implantable processing apparatus is configured to:
    determine positive and negative maximum amplitudes $V_p$ and $V_n$ of said signal of sequential cardiac cycles;
    ascertain an asymmetry factor η of said signal of sequential cardiac cycles according to equation $\eta=V_p-|V_n|)(V_p+|V_n|)$; and
    store said asymmetry factor n of sequential cardiac cycles for analysis.

8. The apparatus according to claim 7 wherein said attachment angle is approximately 45°.

9. The apparatus according to claim 7 wherein said bipolar cardiological measuring electrode is in a ventricle of said heart and wherein an R wave of said intracardiac electrogram is measured with said measuring electrode.

10. The apparatus according to claim 7 wherein said bipolar cardiological measuring electrode is in an atrium of said heart and wherein a P wave of said intracardial electrogram is measured with said measuring electrode.

11. A measuring apparatus for detecting the myocardial state of a heart comprising:
    a bipolar cardiological measuring electrode configured to insert into a heart division and configured to anchor a tip of the electrode in a myocardium of the heart at an attachment angle of less than 90° relative to a myocardial surface;
    an implantable processing apparatus configured to measure a signal of sequential cardiac cycles via intracardiac electrogram to collect measured signals;

a transmitter coupled with said implantable processing apparatus;
an external analysis station;
wherein said transmitter is configured to transmit said measured signals to said external analysis station;
wherein the external analysis station is configured to:
determine positive and negative maximum amplitudes $V_p$ and $V_n$ of said signal of sequential cardiac cycles;
ascertain an asymmetry factor $\eta$ of said signal of sequential cardiac cycles according to equation $\eta=(V_p-|V_n|)/(V_p+|V_n|)$ with said implantable processing apparatus; and
store said asymmetry factor $\eta$ of sequential cardiac cycles for analysis.

12. The apparatus according to claim 11 wherein said attachment angle is approximately 45°.

13. The apparatus according to claim 11 wherein said bipolar cardiological measuring electrode is in a ventricle of said heart and wherein an R wave of said intracardial electrogram is measured with said measuring electrode.

14. The apparatus according to claim 11 wherein said bipolar cardiological measuring electrode is in an atrium of said heart and wherein a P wave of said intracardial electrogram is measured with said measuring electrode.

* * * * *